United States Patent
Ingmanson et al.

(10) Patent No.: US 9,421,014 B2
(45) Date of Patent: Aug. 23, 2016

(54) LOADING UNIT VELOCITY AND POSITION FEEDBACK

(71) Applicant: Covidien LP, Mansfield, MA (US)

(72) Inventors: Michael D. Ingmanson, Stratford, CT (US); Michael A. Zemlok, Prospect, CT (US)

(73) Assignee: Covidien LP, Mansfield, MA (US)

( * ) Notice: Subject to any disclaimer, the term of this patent is extended or adjusted under 35 U.S.C. 154(b) by 479 days.

(21) Appl. No.: 13/955,486

(22) Filed: Jul. 31, 2013

(65) Prior Publication Data

US 2014/0110455 A1  Apr. 24, 2014

Related U.S. Application Data

(60) Provisional application No. 61/715,485, filed on Oct. 18, 2012.

(51) Int. Cl.
*A61B 17/068* (2006.01)
*A61B 17/072* (2006.01)
(Continued)

(52) U.S. Cl.
CPC ......... *A61B 17/068* (2013.01); *A61B 17/07207* (2013.01); *A61B 17/072* (2013.01); *A61B 17/1155* (2013.01); *A61B 2017/00017* (2013.01); *A61B 2017/00119* (2013.01); *A61B 2017/00367* (2013.01); *A61B 2017/00398* (2013.01); *A61B 2017/00464* (2013.01); *A61B 2017/00473* (2013.01); *A61B 2017/00734* (2013.01); *A61B 2017/07271* (2013.01); *A61B 2017/07285* (2013.01)

(58) Field of Classification Search
CPC ........... A61B 17/07207; A61B 17/068; A61B 2017/00398; A61B 2019/4857; A61B 2017/00022

USPC .......................................... 227/175.1, 176.1
See application file for complete search history.

(56) References Cited

U.S. PATENT DOCUMENTS

| | | | |
|---|---|---|---|
| 2,777,340 A | 1/1957 | Hettwer et al. | |
| 2,957,353 A | 10/1960 | Babacz | |
| 3,111,328 A | 11/1963 | Di Rito et al. | |
| 3,695,058 A | 10/1972 | Keith, Jr. | |
| 3,734,515 A | 5/1973 | Dudek | |
| 3,759,336 A | 9/1973 | Marcovitz et al. | |

(Continued)

FOREIGN PATENT DOCUMENTS

| | | |
|---|---|---|
| AU | 2008229795 A1 | 4/2009 |
| CA | 2451558 | 1/2003 |

(Continued)

OTHER PUBLICATIONS

European Examination Report dated Mar. 31, 2015 from EP Application No. 13189026.1.

(Continued)

*Primary Examiner* — Michelle Lopez

(57) ABSTRACT

A loading unit for a surgical stapling device has a cartridge assembly and an anvil assembly, the cartridge assembly including a channel and a staple cartridge having a plurality of surgical staples therein. An axial drive assembly has a clamping member, the clamping member having an upper flange for engaging the anvil assembly, and a lower flange for engaging the channel. The axial drive assembly is movable through the staple cartridge to drive the staples out of the staple cartridge and against the anvil assembly. Mechanical features are defined in the channel for indicating an end of stroke for the axial drive assembly, the mechanical features having a first pattern and a second pattern.

13 Claims, 9 Drawing Sheets

(51) Int. Cl.
  *A61B 17/00* (2006.01)
  *A61B 17/115* (2006.01)

(56) References Cited

U.S. PATENT DOCUMENTS

| | | | |
|---|---|---|---|
| 4,162,399 A | 7/1979 | Hudson |
| 4,606,343 A | 8/1986 | Conta et al. |
| 4,705,038 A | 11/1987 | Sjostrom et al. |
| 4,722,685 A | 2/1988 | de Estrada et al. |
| 4,823,807 A | 4/1989 | Russell et al. |
| 4,874,181 A | 10/1989 | Hsu |
| 5,129,118 A | 7/1992 | Walmesley |
| 5,129,570 A | 7/1992 | Schulze et al. |
| 5,152,744 A | 10/1992 | Krause et al. |
| 5,301,061 A | 4/1994 | Nakada et al. |
| 5,312,023 A | 5/1994 | Green et al. |
| 5,326,013 A | 7/1994 | Green et al. |
| 5,350,355 A | 9/1994 | Sklar |
| 5,383,874 A | 1/1995 | Jackson et al. |
| 5,383,880 A | 1/1995 | Hooven |
| 5,389,098 A | 2/1995 | Tsuruta et al. |
| 5,395,033 A | 3/1995 | Byrne et al. |
| 5,400,267 A | 3/1995 | Denen et al. |
| 5,411,508 A | 5/1995 | Bessler et al. |
| 5,413,267 A | 5/1995 | Solyntjes et al. |
| 5,427,087 A | 6/1995 | Ito et al. |
| 5,467,911 A | 11/1995 | Tsuruta et al. |
| 5,476,379 A | 12/1995 | Disel |
| 5,487,499 A | 1/1996 | Sorrentino et al. |
| 5,518,163 A | 5/1996 | Hooven |
| 5,518,164 A | 5/1996 | Hooven |
| 5,526,822 A | 6/1996 | Burbank et al. |
| 5,529,235 A | 6/1996 | Boiarski et al. |
| 5,535,934 A | 7/1996 | Boiarski et al. |
| 5,535,937 A | 7/1996 | Boiarski et al. |
| 5,540,375 A | 7/1996 | Bolanos et al. |
| 5,540,706 A | 7/1996 | Aust et al. |
| 5,542,594 A | 8/1996 | McKean et al. |
| 5,562,239 A | 10/1996 | Boiarski et al. |
| 5,632,432 A | 5/1997 | Schulze et al. |
| 5,653,374 A | 8/1997 | Young et al. |
| 5,658,300 A | 8/1997 | Bito et al. |
| 5,667,517 A | 9/1997 | Hooven |
| 5,693,042 A | 12/1997 | Boiarski et al. |
| 5,704,534 A | 1/1998 | Huitema et al. |
| 5,713,505 A | 2/1998 | Huitema |
| 5,762,603 A | 6/1998 | Thompson |
| 5,779,130 A | 7/1998 | Alesi et al. |
| 5,782,396 A | 7/1998 | Mastri et al. |
| 5,782,397 A | 7/1998 | Koukline |
| 5,820,009 A | 10/1998 | Melling et al. |
| 5,863,159 A | 1/1999 | Lasko |
| 5,865,361 A | 2/1999 | Milliman et al. |
| 5,908,427 A | 6/1999 | McKean et al. |
| 5,954,259 A | 9/1999 | Viola et al. |
| 5,964,774 A | 10/1999 | McKean et al. |
| 5,993,454 A | 11/1999 | Longo |
| 6,010,054 A | 1/2000 | Johnson et al. |
| 6,017,354 A | 1/2000 | Culp et al. |
| 6,032,849 A | 3/2000 | Mastri et al. |
| 6,045,560 A | 4/2000 | McKean et al. |
| 6,090,123 A | 7/2000 | Culp et al. |
| 6,126,651 A | 10/2000 | Mayer |
| 6,129,547 A | 10/2000 | Cise et al. |
| 6,239,732 B1 | 5/2001 | Cusey |
| 6,241,139 B1 | 6/2001 | Milliman et al. |
| 6,264,086 B1 | 7/2001 | McGuckin, Jr. |
| 6,264,087 B1 | 7/2001 | Whitman |
| 6,302,311 B1 | 10/2001 | Adams et al. |
| 6,315,184 B1 | 11/2001 | Whitman |
| 6,321,855 B1 | 11/2001 | Barnes |
| 6,329,778 B1 | 12/2001 | Culp et al. |
| 6,343,731 B1 | 2/2002 | Adams et al. |
| 6,348,061 B1 | 2/2002 | Whitman |
| 6,368,324 B1 | 4/2002 | Dinger et al. |
| 6,371,909 B1 | 4/2002 | Hoeg et al. |
| 6,434,507 B1 | 8/2002 | Clayton et al. |
| 6,443,973 B1 | 9/2002 | Whitman |
| 6,461,372 B1 | 10/2002 | Jensen et al. |
| 6,488,197 B1 | 12/2002 | Whitman |
| 6,491,201 B1 | 12/2002 | Whitman |
| 6,533,157 B1 | 3/2003 | Whitman |
| 6,537,280 B2 | 3/2003 | Dinger et al. |
| 6,610,066 B2 | 8/2003 | Dinger et al. |
| 6,611,793 B1 | 8/2003 | Burnside et al. |
| 6,645,218 B1 | 11/2003 | Cassidy et al. |
| 6,654,999 B2 | 12/2003 | Stoddard et al. |
| 6,698,643 B2 | 3/2004 | Whitman |
| 6,699,177 B1 | 3/2004 | Wang et al. |
| 6,716,233 B1 | 4/2004 | Whitman |
| 6,783,533 B2 | 8/2004 | Green et al. |
| 6,792,390 B1 | 9/2004 | Burnside et al. |
| 6,793,652 B1 | 9/2004 | Whitman et al. |
| 6,817,508 B1 | 11/2004 | Racenet et al. |
| 6,830,174 B2 | 12/2004 | Hillstead et al. |
| 6,846,308 B2 | 1/2005 | Whitman et al. |
| 6,846,309 B2 | 1/2005 | Whitman et al. |
| 6,849,071 B2 | 2/2005 | Whitman et al. |
| 6,905,057 B2 | 6/2005 | Swayze et al. |
| 6,959,852 B2 | 11/2005 | Shelton, IV et al. |
| 6,964,363 B2 | 11/2005 | Wales et al. |
| 6,981,628 B2 | 1/2006 | Wales |
| 6,981,941 B2 | 1/2006 | Whitman et al. |
| 6,986,451 B1 | 1/2006 | Mastri et al. |
| 6,988,649 B2 | 1/2006 | Shelton, IV et al. |
| 7,032,798 B2 | 4/2006 | Whitman et al. |
| RE39,152 E | 6/2006 | Aust et al. |
| 7,055,731 B2 | 6/2006 | Shelton, IV et al. |
| 7,059,508 B2 | 6/2006 | Shelton, IV et al. |
| 7,077,856 B2 | 7/2006 | Whitman |
| 7,111,769 B2 | 9/2006 | Wales et al. |
| 7,122,029 B2 | 10/2006 | Koop et al. |
| 7,140,528 B2 | 11/2006 | Shelton, IV |
| 7,143,923 B2 | 12/2006 | Shelton, IV et al. |
| 7,143,925 B2 | 12/2006 | Shelton, IV et al. |
| 7,143,926 B2 | 12/2006 | Shelton, IV et al. |
| 7,147,138 B2 | 12/2006 | Shelton, IV |
| 7,172,104 B2 | 2/2007 | Scirica et al. |
| 7,225,964 B2 | 6/2007 | Mastri et al. |
| 7,238,021 B1 | 7/2007 | Johnson |
| 7,246,734 B2 | 7/2007 | Shelton, IV |
| 7,328,828 B2 | 2/2008 | Ortiz et al. |
| 7,364,061 B2 | 4/2008 | Swayze et al. |
| 7,380,695 B2 | 6/2008 | Doll et al. |
| 7,380,696 B2 | 6/2008 | Shelton, IV et al. |
| 7,404,508 B2 | 7/2008 | Smith et al. |
| 7,407,078 B2 | 8/2008 | Shelton, IV et al. |
| 7,416,101 B2 | 8/2008 | Shelton, IV et al. |
| 7,419,080 B2 | 9/2008 | Smith et al. |
| 7,422,139 B2 | 9/2008 | Shelton, IV et al. |
| 7,431,189 B2 | 10/2008 | Shelton, IV et al. |
| 7,441,684 B2 | 10/2008 | Shelton, IV et al. |
| 7,448,525 B2 | 11/2008 | Shelton, IV et al. |
| 7,464,846 B2 | 12/2008 | Shelton, IV et al. |
| 7,464,847 B2 | 12/2008 | Viola et al. |
| 7,464,849 B2 | 12/2008 | Shelton, IV et al. |
| 7,481,347 B2 | 1/2009 | Roy |
| 7,481,824 B2 | 1/2009 | Boudreaux et al. |
| 7,487,899 B2 | 2/2009 | Shelton, IV et al. |
| 7,549,564 B2 | 6/2009 | Boudreaux |
| 7,565,993 B2 | 7/2009 | Milliman et al. |
| 7,568,603 B2 | 8/2009 | Shelton, IV et al. |
| 7,575,144 B2 | 8/2009 | Ortiz et al. |
| 7,588,176 B2 | 9/2009 | Timm et al. |
| 7,637,409 B2 | 12/2009 | Marczyk |
| 7,641,093 B2 | 1/2010 | Doll et al. |
| 7,644,848 B2 | 1/2010 | Swayze et al. |
| 7,670,334 B2 | 3/2010 | Hueil et al. |
| 7,673,780 B2 | 3/2010 | Shelton, IV et al. |
| 7,699,835 B2 | 4/2010 | Lee et al. |
| 7,717,312 B2 * | 5/2010 | Beetel ............... A61B 17/068 227/175.1 |
| 7,721,931 B2 | 5/2010 | Shelton, IV et al. |
| 7,740,159 B2 | 6/2010 | Shelton, IV et al. |

(56) References Cited

U.S. PATENT DOCUMENTS

| | | |
|---|---|---|
| 7,743,960 B2 | 6/2010 | Whitman et al. |
| 7,758,613 B2 | 7/2010 | Whitman |
| 7,766,210 B2 | 8/2010 | Shelton, IV et al. |
| 7,770,773 B2 | 8/2010 | Whitman et al. |
| 7,770,775 B2 | 8/2010 | Shelton, IV et al. |
| 7,793,812 B2 | 9/2010 | Moore et al. |
| 7,799,039 B2 | 9/2010 | Shelton, IV et al. |
| 7,802,712 B2 | 9/2010 | Milliman et al. |
| 7,822,458 B2 | 10/2010 | Webster, III et al. |
| 7,845,534 B2 | 12/2010 | Viola et al. |
| 7,845,537 B2 | 12/2010 | Shelton, IV et al. |
| 7,857,185 B2 | 12/2010 | Swayze et al. |
| 7,870,989 B2 | 1/2011 | Viola et al. |
| 7,905,897 B2 | 3/2011 | Whitman et al. |
| 7,918,230 B2 | 4/2011 | Whitman et al. |
| 7,922,719 B2 | 4/2011 | Ralph et al. |
| 7,947,034 B2 | 5/2011 | Whitman |
| 7,951,071 B2 | 5/2011 | Whitman et al. |
| 7,954,682 B2 | 6/2011 | Giordano et al. |
| 7,959,051 B2 | 6/2011 | Smith et al. |
| 7,963,433 B2 | 6/2011 | Whitman et al. |
| 7,967,178 B2 | 6/2011 | Scirica et al. |
| 7,967,179 B2 | 6/2011 | Olson et al. |
| 7,992,758 B2 | 8/2011 | Whitman et al. |
| 8,016,178 B2 | 9/2011 | Olson et al. |
| 8,016,855 B2 | 9/2011 | Whitman et al. |
| 8,020,743 B2 | 9/2011 | Shelton, IV |
| 8,025,199 B2 | 9/2011 | Whitman et al. |
| 8,052,024 B2 | 11/2011 | Viola et al. |
| 8,056,787 B2 | 11/2011 | Boudreaux et al. |
| 8,114,118 B2 | 2/2012 | Knodel et al. |
| 8,132,705 B2 | 3/2012 | Viola et al. |
| 8,152,516 B2 | 4/2012 | Harvey et al. |
| 8,157,150 B2 | 4/2012 | Viola et al. |
| 8,157,151 B2 | 4/2012 | Ingmanson et al. |
| 8,182,494 B1 | 5/2012 | Yencho et al. |
| 8,186,555 B2 | 5/2012 | Shelton, IV et al. |
| 8,186,587 B2 | 5/2012 | Zmood et al. |
| 8,220,367 B2 | 7/2012 | Hsu |
| 8,235,273 B2 | 8/2012 | Olson et al. |
| 8,241,322 B2 | 8/2012 | Whitman et al. |
| 8,272,554 B2 | 9/2012 | Whitman et al. |
| 8,292,150 B2 | 10/2012 | Bryant |
| 8,292,888 B2 | 10/2012 | Whitman |
| 8,303,581 B2 | 11/2012 | Arts et al. |
| 8,342,379 B2 | 1/2013 | Whitman et al. |
| 8,353,440 B2 | 1/2013 | Whitman et al. |
| 8,357,144 B2 | 1/2013 | Whitman et al. |
| 8,365,633 B2 | 2/2013 | Simaan et al. |
| 8,365,972 B2 | 2/2013 | Aranyi et al. |
| 8,371,492 B2 | 2/2013 | Aranyi et al. |
| 8,372,057 B2 | 2/2013 | Cude et al. |
| 8,391,957 B2 | 3/2013 | Carlson et al. |
| 8,424,739 B2 | 4/2013 | Racenet et al. |
| 8,454,585 B2 | 6/2013 | Whitman |
| 8,505,802 B2 | 8/2013 | Viola et al. |
| 8,517,241 B2 | 8/2013 | Nicholas et al. |
| 8,551,076 B2 | 10/2013 | Duval et al. |
| 8,561,871 B2 | 10/2013 | Rajappa et al. |
| 8,623,000 B2 | 1/2014 | Humayun et al. |
| 8,632,463 B2 | 1/2014 | Drinan et al. |
| 8,647,258 B2 | 2/2014 | Aranyi et al. |
| 8,657,174 B2 | 2/2014 | Yates et al. |
| 8,696,552 B2 | 4/2014 | Whitman |
| 8,708,213 B2 | 4/2014 | Shelton, IV et al. |
| 8,752,749 B2 | 6/2014 | Moore et al. |
| 8,806,973 B2 | 8/2014 | Ross et al. |
| 8,851,355 B2 | 10/2014 | Aranyi et al. |
| 8,858,571 B2 | 10/2014 | Shelton, IV et al. |
| 8,967,443 B2 | 3/2015 | McCuen |
| 2003/0038938 A1 | 2/2003 | Jung et al. |
| 2004/0111012 A1 | 6/2004 | Whitman |
| 2004/0133189 A1 | 7/2004 | Sakurai |
| 2004/0176751 A1 | 9/2004 | Weitzner et al. |
| 2005/0131442 A1 | 6/2005 | Yachia et al. |
| 2006/0142656 A1 | 6/2006 | Malackowski et al. |
| 2006/0278680 A1 | 12/2006 | Viola et al. |
| 2007/0023477 A1 | 2/2007 | Whitman et al. |
| 2007/0029363 A1 | 2/2007 | Popov |
| 2007/0055219 A1 | 3/2007 | Whitman et al. |
| 2007/0084897 A1 | 4/2007 | Shelton et al. |
| 2007/0102472 A1 | 5/2007 | Shelton |
| 2007/0152014 A1 | 7/2007 | Gillum et al. |
| 2007/0175949 A1 | 8/2007 | Shelton et al. |
| 2007/0175950 A1 | 8/2007 | Shelton et al. |
| 2007/0175951 A1 | 8/2007 | Shelton et al. |
| 2007/0175955 A1 | 8/2007 | Shelton et al. |
| 2007/0175961 A1 | 8/2007 | Shelton et al. |
| 2008/0029570 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0058801 A1 | 3/2008 | Taylor et al. |
| 2008/0109012 A1 | 5/2008 | Falco et al. |
| 2008/0110958 A1 | 5/2008 | McKenna et al. |
| 2008/0185419 A1 | 8/2008 | Smith et al. |
| 2008/0188841 A1 | 8/2008 | Tomasello et al. |
| 2008/0197167 A1 | 8/2008 | Viola et al. |
| 2008/0208195 A1 | 8/2008 | Shores et al. |
| 2008/0251561 A1 | 10/2008 | Eades et al. |
| 2008/0255413 A1 | 10/2008 | Zemlok et al. |
| 2008/0255607 A1 | 10/2008 | Zemlok |
| 2008/0262654 A1 | 10/2008 | Omori et al. |
| 2008/0308603 A1 | 12/2008 | Shelton et al. |
| 2009/0090763 A1 | 4/2009 | Zemlok et al. |
| 2009/0099876 A1 | 4/2009 | Whitman |
| 2009/0171147 A1 | 7/2009 | Lee et al. |
| 2009/0182193 A1 | 7/2009 | Whitman et al. |
| 2009/0209990 A1 | 8/2009 | Yates et al. |
| 2009/0254094 A1 | 10/2009 | Knapp et al. |
| 2010/0069942 A1 | 3/2010 | Shelton, IV |
| 2010/0225073 A1 | 9/2010 | Porter et al. |
| 2011/0006101 A1 | 1/2011 | Hall et al. |
| 2011/0017801 A1 | 1/2011 | Zemlok et al. |
| 2011/0077673 A1 | 3/2011 | Grubac et al. |
| 2011/0121049 A1 | 5/2011 | Malinouskas et al. |
| 2011/0125138 A1 | 5/2011 | Malinouskas et al. |
| 2011/0139851 A1 | 6/2011 | McCuen |
| 2011/0155783 A1 | 6/2011 | Rajappa et al. |
| 2011/0174099 A1 | 7/2011 | Ross et al. |
| 2011/0204119 A1 | 8/2011 | McCuen |
| 2011/0218522 A1 | 9/2011 | Whitman |
| 2011/0253765 A1 | 10/2011 | Nicholas et al. |
| 2011/0290854 A1 | 12/2011 | Timm et al. |
| 2011/0295242 A1 | 12/2011 | Spivey et al. |
| 2011/0295269 A1 | 12/2011 | Swensgard et al. |
| 2012/0000962 A1 | 1/2012 | Racenet et al. |
| 2012/0089131 A1 | 4/2012 | Zemlok et al. |
| 2012/0143002 A1 | 6/2012 | Aranyi et al. |
| 2012/0172924 A1 | 7/2012 | Allen, IV |
| 2012/0223121 A1 | 9/2012 | Viola et al. |
| 2012/0253329 A1 | 10/2012 | Zemlok et al. |
| 2012/0310220 A1 | 12/2012 | Malkowski et al. |
| 2012/0323226 A1 | 12/2012 | Chowaniec et al. |
| 2013/0018361 A1 | 1/2013 | Bryant |
| 2013/0098966 A1 | 4/2013 | Kostrzewski et al. |
| 2013/0098968 A1 | 4/2013 | Aranyi et al. |
| 2013/0098969 A1 | 4/2013 | Scirica et al. |
| 2013/0214025 A1 | 8/2013 | Zemlok et al. |
| 2013/0240596 A1 | 9/2013 | Whitman |
| 2013/0274722 A1 | 10/2013 | Kostrzewski et al. |
| 2013/0282052 A1 | 10/2013 | Aranyi et al. |
| 2013/0292451 A1 | 11/2013 | Viola et al. |
| 2013/0313304 A1 | 11/2013 | Shelton, IV et al. |
| 2013/0317486 A1 | 11/2013 | Nicholas et al. |
| 2014/0110455 A1 | 4/2014 | Ingmanson et al. |
| 2014/0207182 A1 | 7/2014 | Zergiebel et al. |
| 2014/0236173 A1 | 8/2014 | Scirica et al. |
| 2014/0236174 A1 | 8/2014 | Williams et al. |
| 2014/0276932 A1 | 9/2014 | Williams et al. |
| 2014/0299647 A1 | 10/2014 | Scirica et al. |
| 2014/0303668 A1 | 10/2014 | Nicholas et al. |
| 2014/0358129 A1 | 12/2014 | Zergiebel et al. |
| 2014/0361068 A1 | 12/2014 | Aranyi et al. |

(56) References Cited

U.S. PATENT DOCUMENTS

| | | |
|---|---|---|
| 2014/0373652 A1 | 12/2014 | Zergiebel et al. |
| 2015/0048144 A1 | 2/2015 | Whitman |
| 2015/0076205 A1 | 3/2015 | Zergiebel |
| 2015/0080912 A1 | 3/2015 | Sapre |

FOREIGN PATENT DOCUMENTS

| | | | |
|---|---|---|---|
| CN | 101856251 A | 10/2010 | |
| CN | 102 247 182 | 11/2011 | |
| DE | 102008053842 A1 | 5/2010 | |
| EP | 0634144 A1 | 1/1995 | |
| EP | 0648476 A1 | 4/1995 | |
| EP | 0686374 A2 | 12/1995 | |
| EP | 0705571 A1 | 4/1996 | |
| EP | 1690502 A1 | 8/2006 | |
| EP | 1723913 A1 | 11/2006 | |
| EP | 1736112 A1 | 12/2006 | |
| EP | 1759652 A2 | 3/2007 | |
| EP | 1769754 A1 | 4/2007 | |
| EP | 1772105 A1 | 4/2007 | |
| EP | 1 813 203 A2 | 8/2007 | |
| EP | 1813199 | 8/2007 | |
| EP | 1813211 | 8/2007 | |
| EP | 1908412 A2 | 4/2008 | |
| EP | 1917929 A1 | 5/2008 | |
| EP | 1943954 A2 | 7/2008 | |
| EP | 1943956 A2 | 7/2008 | |
| EP | 1943958 A1 | 7/2008 | |
| EP | 1943976 A2 | 7/2008 | |
| EP | 1952769 A2 | 8/2008 | |
| EP | 2 005 898 | 12/2008 | |
| EP | 2027819 A1 | 2/2009 | |
| EP | 2044890 A1 | 4/2009 | |
| EP | 2055243 A2 | 5/2009 | |
| EP | 2090247 A1 | 8/2009 | |
| EP | 2098170 A2 | 9/2009 | |
| EP | 2100561 A2 | 9/2009 | |
| EP | 2100562 A2 | 9/2009 | |
| EP | 2165664 A2 | 3/2010 | |
| EP | 2236098 | 10/2010 | |
| EP | 2245994 A1 | 11/2010 | |
| EP | 2263568 | 12/2010 | |
| EP | 2272443 A1 | 1/2011 | |
| EP | 2316345 A1 | 5/2011 | |
| EP | 2324776 A2 | 5/2011 | |
| EP | 2329773 | 6/2011 | |
| EP | 2333509 A1 | 6/2011 | |
| EP | 2377472 A1 | 10/2011 | |
| EP | 2462878 A1 | 6/2012 | |
| EP | 2462880 A2 | 6/2012 | |
| EP | 2491872 A1 | 8/2012 | |
| EP | 2586382 | 5/2013 | |
| EP | 2606834 | 6/2013 | |
| EP | 2676615 A2 | 12/2013 | |
| EP | 2815705 A1 | 12/2014 | |
| ES | 2333509 A1 | 2/2010 | |
| FR | 2861574 A1 | 5/2005 | |
| JP | 08-038488 | 2/1996 | |
| JP | 2005-125075 A | 5/2005 | |
| WO | 99/15086 A1 | 4/1999 | |
| WO | 00/72760 A1 | 12/2000 | |
| WO | 00/72765 A1 | 12/2000 | |
| WO | WO 03/000138 | 1/2003 | |
| WO | 03/026511 A1 | 4/2003 | |
| WO | 03/030743 A2 | 4/2003 | |
| WO | 03065916 A1 | 8/2003 | |
| WO | 03/077769 A1 | 9/2003 | |
| WO | 03090630 A2 | 11/2003 | |
| WO | 2004/107989 A1 | 12/2004 | |
| WO | 2006/042210 A2 | 4/2006 | |
| WO | 2007016290 A2 | 2/2007 | |
| WO | 2007/026354 A1 | 3/2007 | |
| WO | 2007137304 A2 | 11/2007 | |
| WO | 2008/131362 A2 | 10/2008 | |
| WO | 2008/133956 A2 | 11/2008 | |
| WO | 2009039506 A1 | 3/2009 | |
| WO | 2007014355 A3 | 4/2009 | |
| WO | 2009/132359 A2 | 10/2009 | |
| WO | 2009/143092 A1 | 11/2009 | |
| WO | 2009149234 A1 | 12/2009 | |
| WO | WO 2011/108840 | 9/2011 | |
| WO | 2012040984 A1 | 4/2012 | |

OTHER PUBLICATIONS

International Search Report corresponding to PCT/US2005/027266, completed May 30, 2008 and mailed Jun. 18, 2008; (2 pp.).
Extended European Search Report corresponding to EP 08 25 3184.9, completed Feb. 12, 2009 and mailed Feb. 27, 2009; (3 pp.).
Extended European Search Report corresponding to EP 10 25 0228.3, completed May 20, 2010 and mailed Jun. 1, 2010; (6 pp.).
Extended European Search Report corresponding to EP 10 25 2037.6, completed Mar. 1, 2011 and mailed Mar. 9, 2011; (3 pp.).
Extended European Search Report corresponding to EP 10 25 1968.3, completed on Jul. 4, 2011 and mailed Jul. 14, 2011; (12 pp.).
Extended European Search Report corresponding to EP 11 15 2266.0, completed Jul. 15, 2011 and mailed Jul. 28, 2011; (3 pp.).
Extended European Search Report corresponding to EP 11 25 0462.6, completed Jul. 20, 2011 and mailed Jul. 28, 2011; (6 pp.).
Extended European Search Report corresponding to EP 11 25 0771.0, completed Feb. 7, 2012 and mailed Feb. 17, 2012; (3 pp.).
Extended European Search Report corresponding to EP 06 78 8914.7, completed May 3, 2012 and mailed May 11, 2012; (8 pp.).
Partial European Search Report corresponding to EP 12 18 6177.7, completed Jan. 30, 2013 and mailed Feb. 12, 2013; (6 pp.).
Extended European Search Report corresponding to EP 08 25 2703.7, completed Oct. 23, 2008 and mailed Oct. 31, 2008; (7 pp.).
Extended European Search Report dated Jun. 1, 2015 from Application No. EP 15156035.6.
Extended European Search Report from EP Application No. 13189026.1 dated Jan. 31, 2014.
Extended European Search Report corresponding to EP No. 11 17 8021.9, mailed Jun. 4, 2013; (3 pp).
Extended European Search Report corresponding to EP No. 13 16 3033.7, completed Jun. 27, 2013 and mailed Jul. 15, 2013; (8 pp).
Extended European Search Report corresponding to EP No. 12 18 6177.7, completed Aug. 14, 2013 and mailed Aug. 23, 2013; (8 pp).
Partial European Search Report corresponding to EP No. 13 17 1742.3, completed Sep. 17, 2013 and mailed Sep. 25, 2013; (8 pp).
Partial European Search Report corresponding to EP No. 13 17 2400.7, completed Sep. 18, 2013 and mailed Oct. 1, 2013; (7 pp).
Extended European Search Report corresponding to EP No. 13 17 5475.6, completed Sep. 23, 2013 and mailed Oct. 1, 2013; (8 pp).
Extended European Search Report corresponding to EP No. 13 17 5478.0, completed Sep. 24, 2013 and mailed Oct. 2, 2013; (6 pp).
Extended European Search Report corresponding to EP No. 13 17 5479.8, completed Sep. 27, 2013 and mailed Oct. 10, 2013; (7 pp).
Partial European Search Report corresponding to EP No. 13 17 5477.2, completed Oct. 7, 2013 and mailed Oct. 15, 2013; (7 pp).
Extended European Search Report corresponding to EP No. 08 25 2703.7, completed Oct. 23, 2008 and mailed Oct. 31, 2008; (7 pp).
European search Report from Appl. No. 13177163.6 dated Nov. 15, 2013. (8 pp).
Extended European Search Report from EP Application No. 13172400.7 dated Jan. 21, 2014.
The extended European Search Report from Application No. EP 13177163.6 dated Feb. 6, 2014.
Extended European Search Report from Application No. EP 13175477.2 dated Feb. 6, 2014.
Extended European Search Report from Application No. EP 13169998.5 dated Feb. 24, 2014.
Extended European Search Report corresponding to EP 13176805.3, dated Nov. 4, 2013.
Extended European Search Report from Application No. EP 13171742.3 dated Jan. 3, 2014.

* cited by examiner

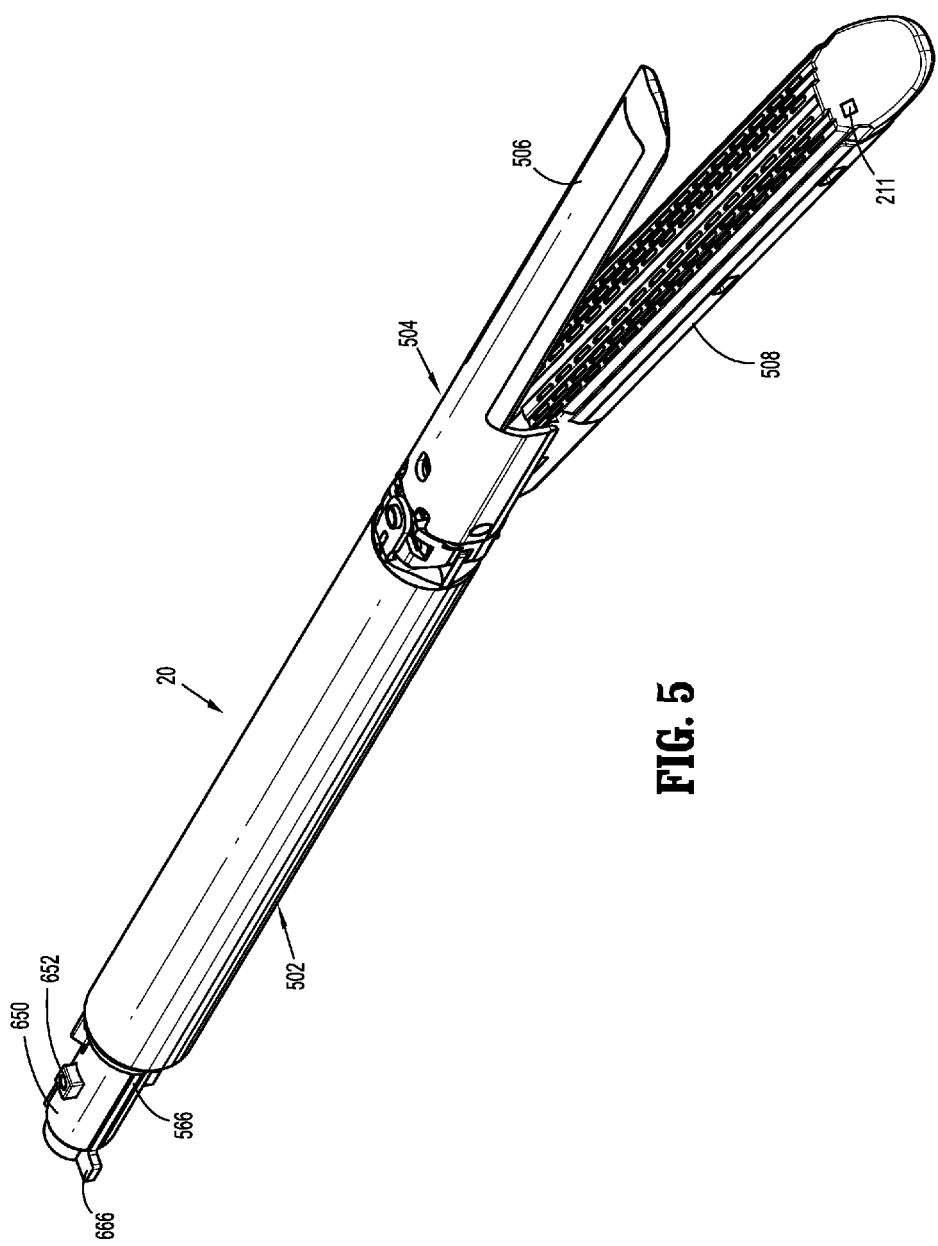

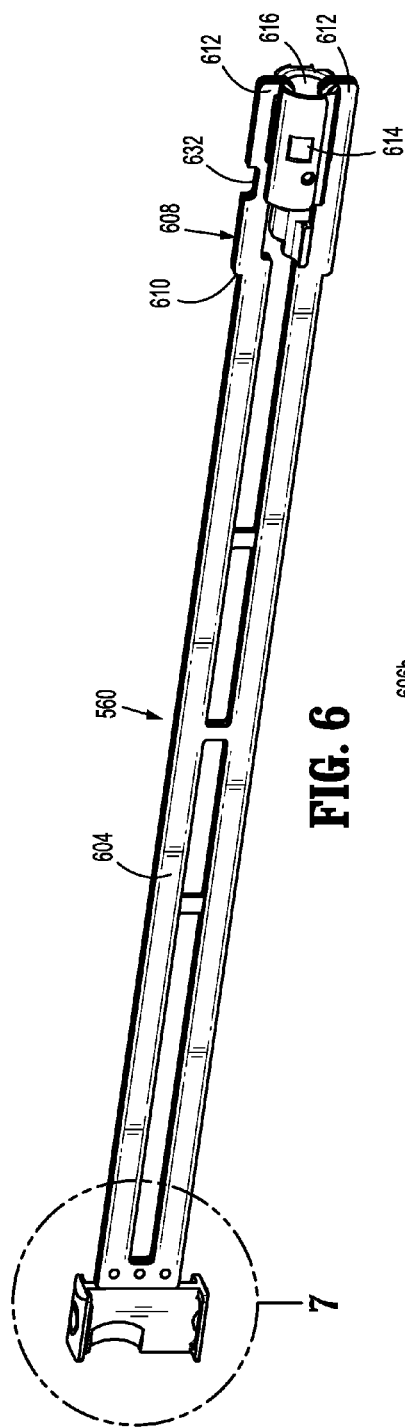
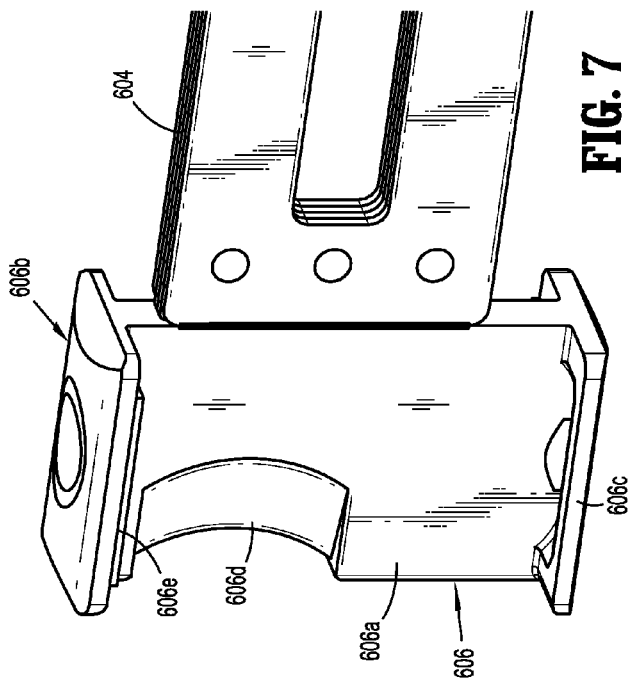

LOADING UNIT VELOCITY AND POSITION FEEDBACK

CROSS-REFERENCE TO RELATED APPLICATIONS

This application claims the benefit of and priority to U.S. Provisional Patent Application No. 61/715,485, filed Oct. 18, 2012, the entire disclosure of which is incorporated by reference herein.

TECHNICAL FIELD

The present disclosure is directed to surgical devices, such as surgical stapling instruments, that have a handle portion and a removable and replaceable end effector or loading unit. In particular, the present disclosure relates to surgical devices and loading units having sensors for identifying the type of end effector, and providing feedback concerning the use of the loading unit.

BACKGROUND

Surgical devices having a handle portion and a replaceable unit are known. A surgical device that can be used to fire different types and sizes of loading units is disclosed in U.S. Pat. No. 7,044,353 to Mastri et al. ("Mastri"), the disclosure of which is hereby incorporated by reference in its entirety. In Mastri, the loading units can have different sized surgical staples and, further, different staple line lengths. U.S. Pat. No. 7,565,993 to Milliman et al. discloses articulating and non-articulating loading units that can be used with a handle portion, the disclosure of which is hereby incorporated by reference in its entirety.

Surgical devices having an adapter assembly and a plurality of surgical end effectors that can be attached thereto are disclosed in U.S. Publication No. 2011-0174099, which is hereby incorporated by reference in its entirety. The adapter is used to enable a powered motorized hand held driver to connect to a variety of end effectors, such as an end to end anastomosis end effector, or circular stapler, an endoscopic gastrointestinal anastomosis end effector, such as a linear endoscopic stapler, or a transverse anastomosis end effector. Powered surgical devices having a remote power console have also been proposed, as disclosed by U.S. Pat. No. 6,846,307 to Whitman et al. ("Whitman"), which is hereby incorporated by reference in its entirety. Whitman discloses a controller in the console for controlling the surgical device. The controller can have a memory unit, including RAM and ROM, and reads data from the particular end effector attached to the controller. The controller can read identification data from a memory unit on the end effector attached to the controller and then, by virtue of the controller's connection to the motors of the surgical device, control the operation of the surgical device.

A powered surgical instrument is disclosed by U.S. Pat. No. 7,887,530 to Zemlok et al., the entire disclosure of which is hereby incorporated by reference herein, utilizes a shift motor to drive multiple functions of the instrument. A variety of sensors is disclosed.

In the context of surgical devices designed to be used with a variety of removable and replaceable end effectors or loading units, it is desirable to identify the type of end effector or loading unit that is attached. This information can be used to determine how to operate the surgical device.

SUMMARY

A loading unit for a surgical stapling device comprises a cartridge assembly and an anvil assembly, the cartridge assembly including a channel and a staple cartridge having a plurality of surgical staples therein. The loading unit has an axial drive assembly with a clamping member, the clamping member having an upper flange for engaging the anvil assembly, and a lower flange for engaging the channel, the axial drive assembly being movable through the staple cartridge to drive the staples out of the staple cartridge and against the anvil assembly. Mechanical features are defined in the channel for indicating an end of stroke for the axial drive assembly, the mechanical features having a first pattern and a second pattern.

The staple cartridge of the loading unit can have a plurality of staple retaining recesses and the surgical staples are disposed in the staple retaining recesses. In certain embodiments, the staple retaining recesses are arranged in linear rows. The axial drive assembly can include a drive beam.

In certain embodiments, a sensor is included for determining a gap between the anvil assembly and the cartridge assembly.

A surgical stapling device, comprising an elongate portion and a loading unit. The loading unit comprises a cartridge assembly and an anvil assembly, the cartridge assembly including a channel and a staple cartridge having a plurality of surgical staples therein. The loading unit has an axial drive assembly with a clamping member, the clamping member having an upper flange for engaging the anvil assembly, and a lower flange for engaging the channel, the axial drive assembly being movable through the staple cartridge to drive the staples out of the staple cartridge and against the anvil assembly. Mechanical features are defined in the channel for indicating an end of stroke for the axial drive assembly, the mechanical features having a first pattern and a second pattern.

The surgical stapling device can further comprise a handle portion. The surgical stapling device handle portion can have a motor assembly. The surgical stapling device can comprise a controller. The surgical stapling device controller can be configured to determine the end of stroke. The surgical stapling device can have the first pattern of mechanical features with mechanical features of a different size than a size of the mechanical features of the second pattern.

The staple cartridge of the loading unit can define a longitudinal axis and staple retaining recesses arranged in linear rows along the longitudinal axis. The channel of the cartridge assembly can define a slot. A distal end of the slot may form the end of stroke.

The second pattern of mechanical features can be closer to the distal end of the slot than the first pattern of mechanical features. In certain embodiments, a light sensor detects the mechanical features.

BRIEF DESCRIPTION OF THE DRAWINGS

Embodiments of the presently disclosed surgical device are disclosed herein, with reference to the following drawings:

FIG. 5 is a perspective view of a loading unit according to certain embodiments of the present disclosure;

FIG. 6 is an axial drive assembly for a loading unit according to certain embodiments of the present disclosure;

FIG. 7 is a detailed view of the clamping member of the axial drive assembly in accordance with certain embodiments of the present disclosure;

DETAILED DESCRIPTION

Figure 1:
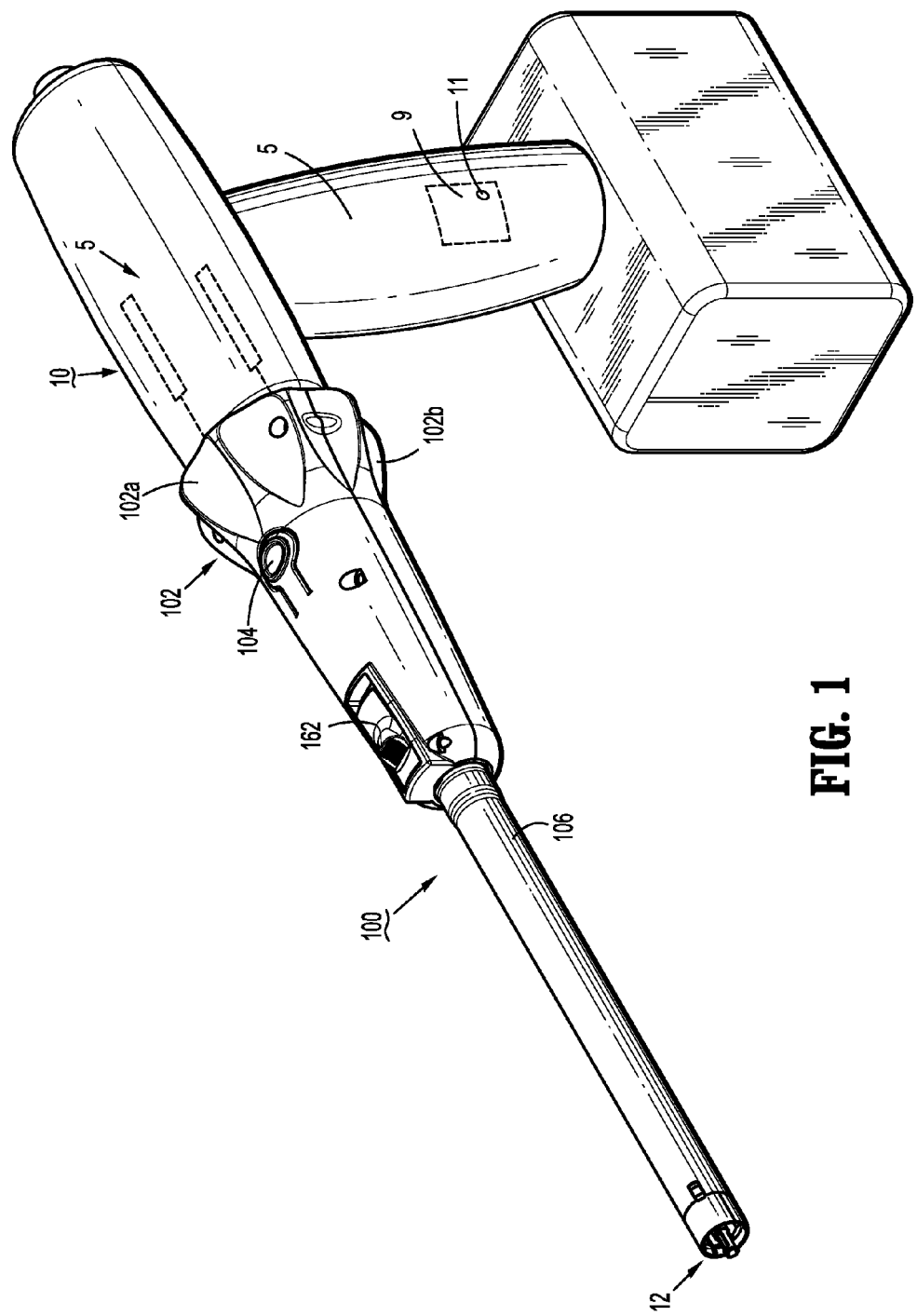
FIG. 1 is a perspective view of the handle portion according to certain embodiments of the disclosure.
Figure 1A:
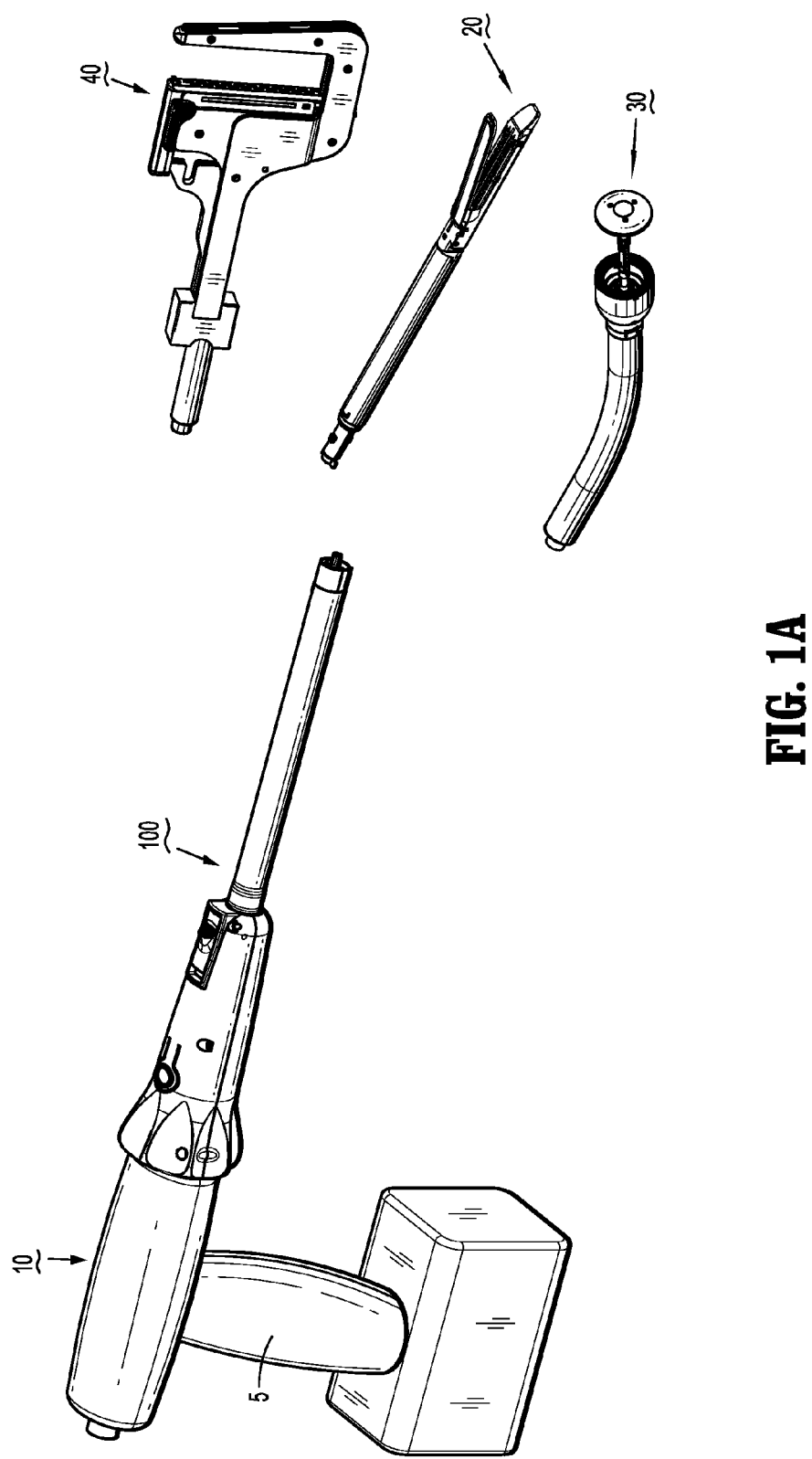
FIG. 1A is a perspective view of a handle portion and loading units according to certain embodiments of the disclosure.
Figure 2:
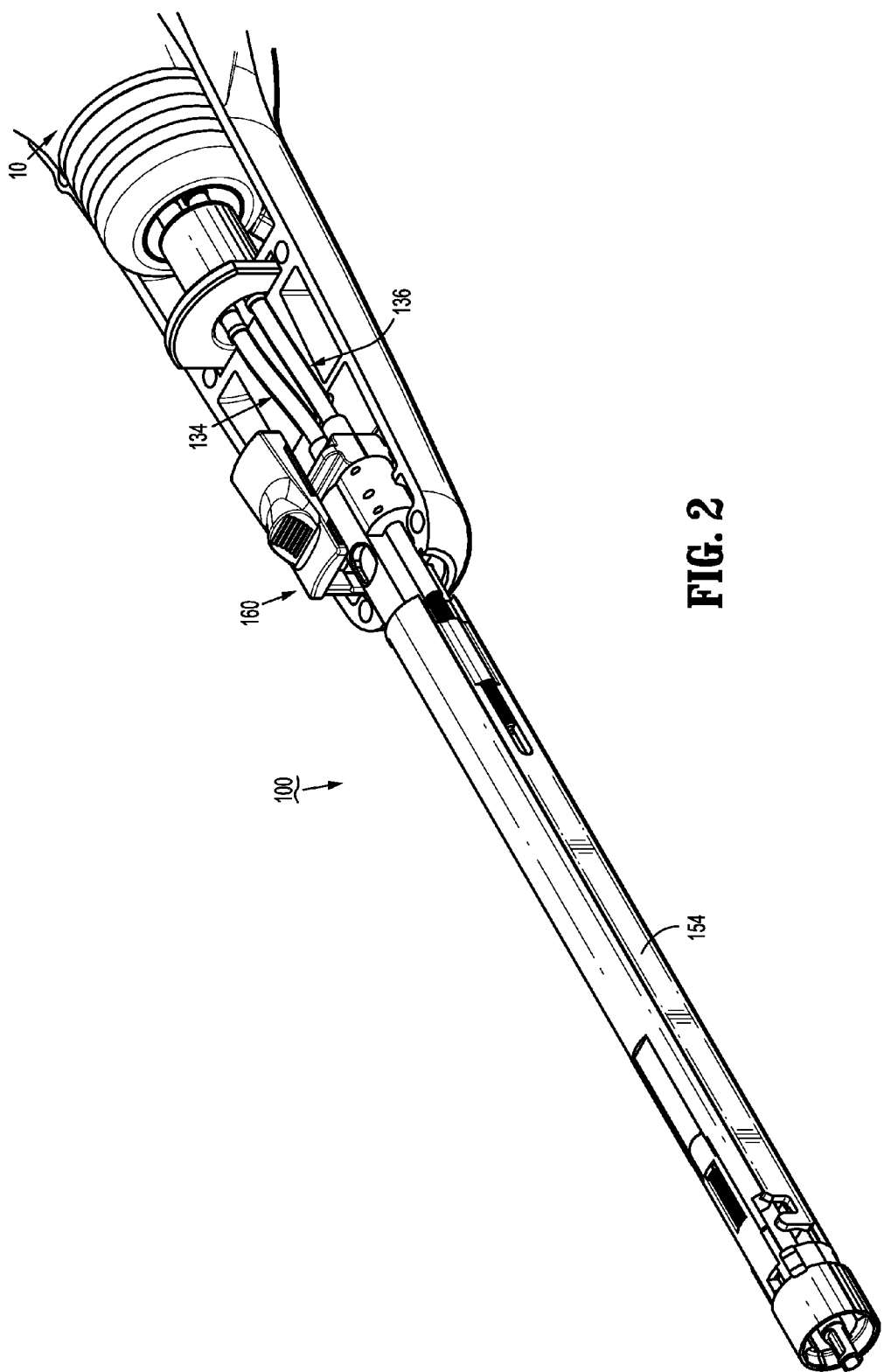
FIG. 2 is a perspective view of an adapter attached to a handle portion, with some parts removed according to certain embodiments of the disclosure.

Persons having skill in the art will understand the present invention from reading the following description in conjunction with the accompanying drawings. Reference characters indicate the same or similar elements throughout the drawings. As is customary, the term "distal" refers to a location farther from the user of the instrument and the term "proximal" refers to a location that is closer to the user of the instrument.

A surgical device having a handle portion 10, and a plurality of removable and replaceable loading units, is shown in FIGS. 1 through 9. The surgical device includes an elongate portion. For example, the handle portion 10 may have an endoscopic shaft that forms part of the handle portion 10 or the handle portion 10 may be connected to an adapter assembly 100 that includes an outer tube 106 and release button 104 having a latch for removably connecting the adapter assembly to the handle portion 10. Alternatively, the connection can be a threaded connection, bayonet connection or any other connection. In any of the embodiments disclosed herein, a plurality of different adapters may be provided, to work in conjunction with a plurality of different handle portions and/or a plurality of different end effectors, to provide a versatile surgical system. For example, adapter assemblies can be provided with different length shafts, or shafts with different shapes such as curved or straight. Adapter assemblies can be provided to connect to different surgical end effectors, such as electrosurgical instruments, circular staplers, linear endoscopic staplers, etc.

The distal end of the endoscopic shaft, or the distal end of the adapter assembly 100, has a connection portion 12 for forming a connection to a loading unit. Loading units 20, 30 and 40 are shown. Although a linear endoscopic stapling loading unit 20 is described in detail, a circular stapling 30 or a transverse stapling 40 loading unit may also be attached to the surgical device. Loading units incorporating electrical energy, ultrasonic energy, or other energy can also be provided. Appropriate adapter assemblies are provided to accommodate the various loading units. For example, it may be desirable to provide three drive shafts for operating the circular stapling loading unit 30. An adapter assembly having three drive shafts therein could be used to separately drive the opening and closing of the anvil to grasp tissue, the driving of the staples through tissue and against the anvil, and the cutting of tissue.

Figure 3:
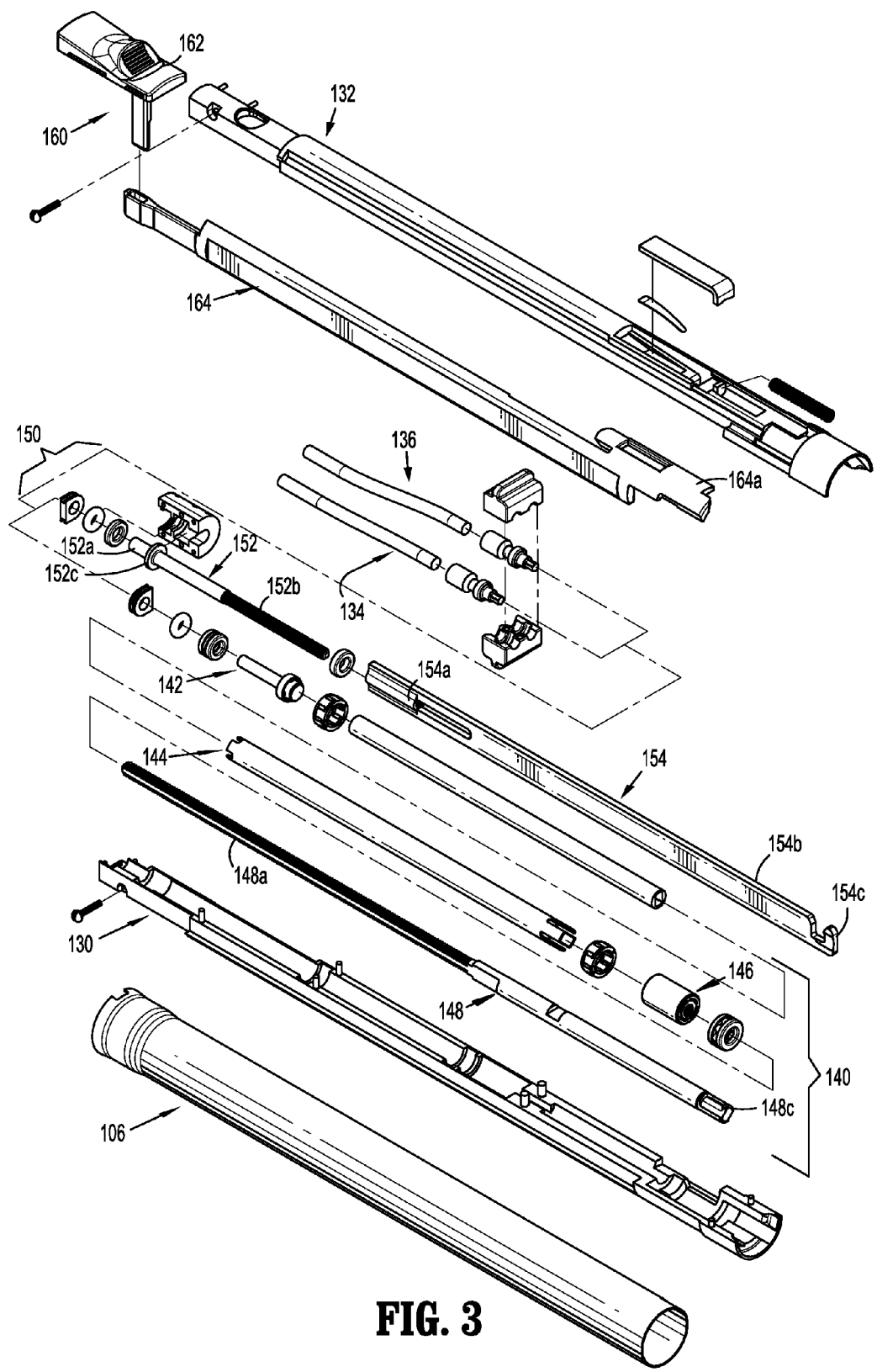
FIG. 3 is an exploded perspective view of an adapter according to certain embodiments of the disclosure.
Figure 4:
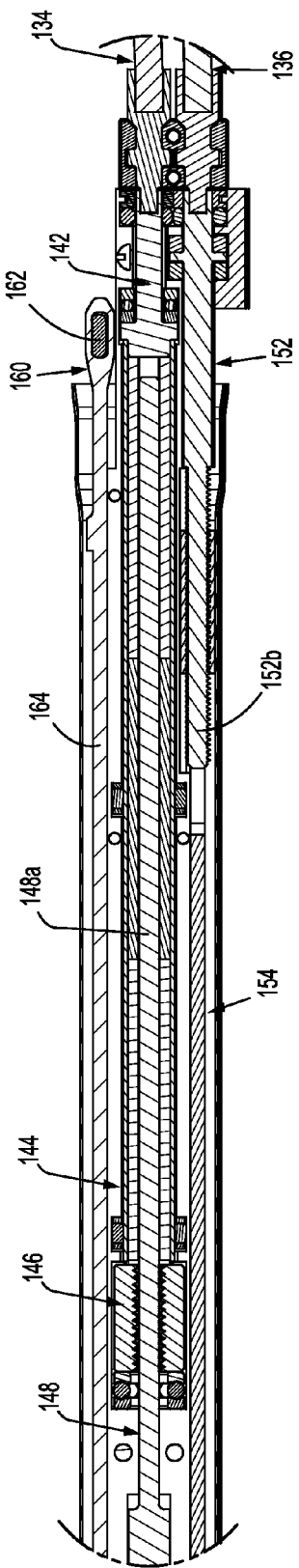
FIG. 4 is a cross sectional view of part of an adapter according to certain embodiments of the disclosure.

The adapter assembly 100 that is used with the loading unit 20 has a body 130 and two drivers: an articulation drive cable 136 and a stapling drive cable 134. As best seen in FIG. 3, the adapter assembly 100 has a drive converter assembly for each of the drive shafts, to convert rotational motion of the output from the motor assembly 5 to linear translation of the drive members of the adapter assembly. For example, the first drive converter assembly 150 has a first shaft 152 that connects to a first output from the motor assembly 5 via the drive cable 136. The first shaft 152 includes a threaded distal end 152b. The articulation drive bar 154 has an internally threaded collar 154a that is engaged with the threaded distal end of the first shaft 152. The threaded distal end 154b is long enough to translate the articulation drive bar 154 a desired distance.

The second drive converter assembly 140 has a second shaft 148 that connects to a second output from the motor assembly 5, through the stapling drive cable 134. The second shaft 148 includes a threaded proximal end 148a. An internally threaded collar 146 is engaged with the threaded proximal end 148a of the second shaft. The collar 146 is connected to a tubular sleeve 144. A proximal coupling 142 connects the drive cable 134 to the tubular sleeve 144. As the drive cable 134 rotates, the tubular sleeve 144 and collar 146 are rotated and the second shaft 148 is advanced in a distal direction. The threaded proximal end 148a is long enough to translate the second or stapling drive shaft 148 a desired distance for clamping of tissue and firing staples. In any of the embodiments disclosed herein, the drive converter assembly can have shafts that are internally threaded and the articulation drive shaft and/or stapling drive shaft can have an end that forms a threaded rod to engage and interact with the internally threaded member.

The motor assembly 5 can be separate from the surgical device, but is desirably part of the handle portion 10. One or more motors are used. For example, two dual directional motors can be mounted in the handle portion 10 and connected to a power source which may be a battery internal or external to the handle portion 10. It is contemplated that the power source can be a tethered power source such as a generator or electrical outlet connection, and the handle can lack a battery or include a battery in addition to the other power source. Each motor can be connected to a switch on the handle portion and an additional switch for reversing the direction of the motors can be provided on the handle portion as well. The power source is desirably a removable and rechargeable direct current battery, but alternative sources, such as a remote access outlet for alternating current supply, can be used. A transformer or gear set can be used to adapt the power source for the motors.

The distal end of the adapter assembly 100 has a connection portion 12 for removably connecting to the loading unit 20. The connection portion 12 may essentially form a bayonet connection, like that described in U.S. Pat. No. 7,044,353 to Mastri et al. ("Mastri"), the disclosure of which is hereby incorporated by reference herein in its entirety. A locking member 164 for securing the loading unit 20 unto the adapter assembly 100 is connected to a button 162. The button 162 is spring biased to a locked position to prevent removal of the loading unit until the button is moved to an unlocked position.

The endoscopic linear stapling loading unit can be like those described in Mastri or Millman et al., U.S. Pat. No. 7,565,993, the entire disclosures of which are hereby incorporated by reference herein. The loading unit may also be as described in Surgical Device Identification, filed on the same day herewith, the entire disclosure of which is hereby incorporated by reference herein. The loading unit 20 has an elongate body portion 502 with a proximal end 650 defining two lugs 652 for forming a connection with a shaft of an adapter assembly 100 or a handle portion. Other means of connecting the loading unit can be used. The loading units can be designed to be attached to either a powered, motorized surgical driver or manually actuated handle. An end 164a of the locking member 164 of the connection portion of the adapter assembly 100 (see FIG. 3) engages the lugs 652 of the loading unit to secure it in place. A tube 602 is disposed around the body 502.

The loading unit 20 has an articulation link 566 with a hooked proximal end 666 for engaging a hooked distal end 154c of the articulation drive bar 154. An axial drive assembly 560 has a proximal pusher 614 for engaging the stapling drive shaft 148. Each of the stapling drive shaft 148 and articulation drive bar 154 are driven by their respective outputs from the motor assembly and, by virtue of the drive converter assemblies, are translated axially in a distal direction.

The axial drive assembly 560 has a stapling drive member or drive beam 604 and clamping member 606 at a distal end of the drive beam 604. (See FIG. 8). The drive beam 604 may be an elongate sheet of material or a series of stacked sheets of material. The clamping member 606 is a member that has an upper flange 606b and a lower flange 606c (see FIG. 7) attached to a vertical portion 606a that has a knife blade. The clamping member 606 is attached to the drive beam or drive member 604 by welding, adhesive, or some other method. The proximal portion of the drive beam 604 has an opening for carrying the pusher 614 so that the stapling drive shaft 148 will drive movement of the axial drive assembly distally. The clamping member 606 may have molded pieces of plastic, or another plastic coating, for reducing the friction that will occur during clamping and stapling. See EP 1,908,414 and U.S. Publication No. 2008/0083812, the entire disclosures of which are hereby incorporated by reference herein.

A pair of jaws 506, 508 are attached to the elongate body 502 via a mounting portion 572. A stapler anvil assembly 506 includes an anvil 512 and cover 510. The anvil 512 defines a slot to allow the passage of the axial drive assembly. The cartridge assembly 508 includes a staple cartridge 518, channel 516 and a firing assembly for interacting with the drive beam 604 and clamping member 606. The channel has a ramped or sloping surface 516a. The channel 516 also defines a slot (not shown) that allows the vertical portion 606a to extend through the slot and locate the lower flange 606c below the channel 516. The staple cartridge 518 defines a plurality of staple slots 528 and a slot 526 corresponding to the slots in the channel 516 and anvil 512.

The anvil assembly, cartridge assembly, or both, are pivotably movable. For example, the channel 516 has a proximal end with two holes 580 for receiving bolts 582. The bolts extend through mounting assembly 572 so that the cartridge assembly can pivot with respect to the anvil assembly. In this way, tissue can be clamped between the anvil assembly 207 and the cartridge assembly 230.

Figure 8:
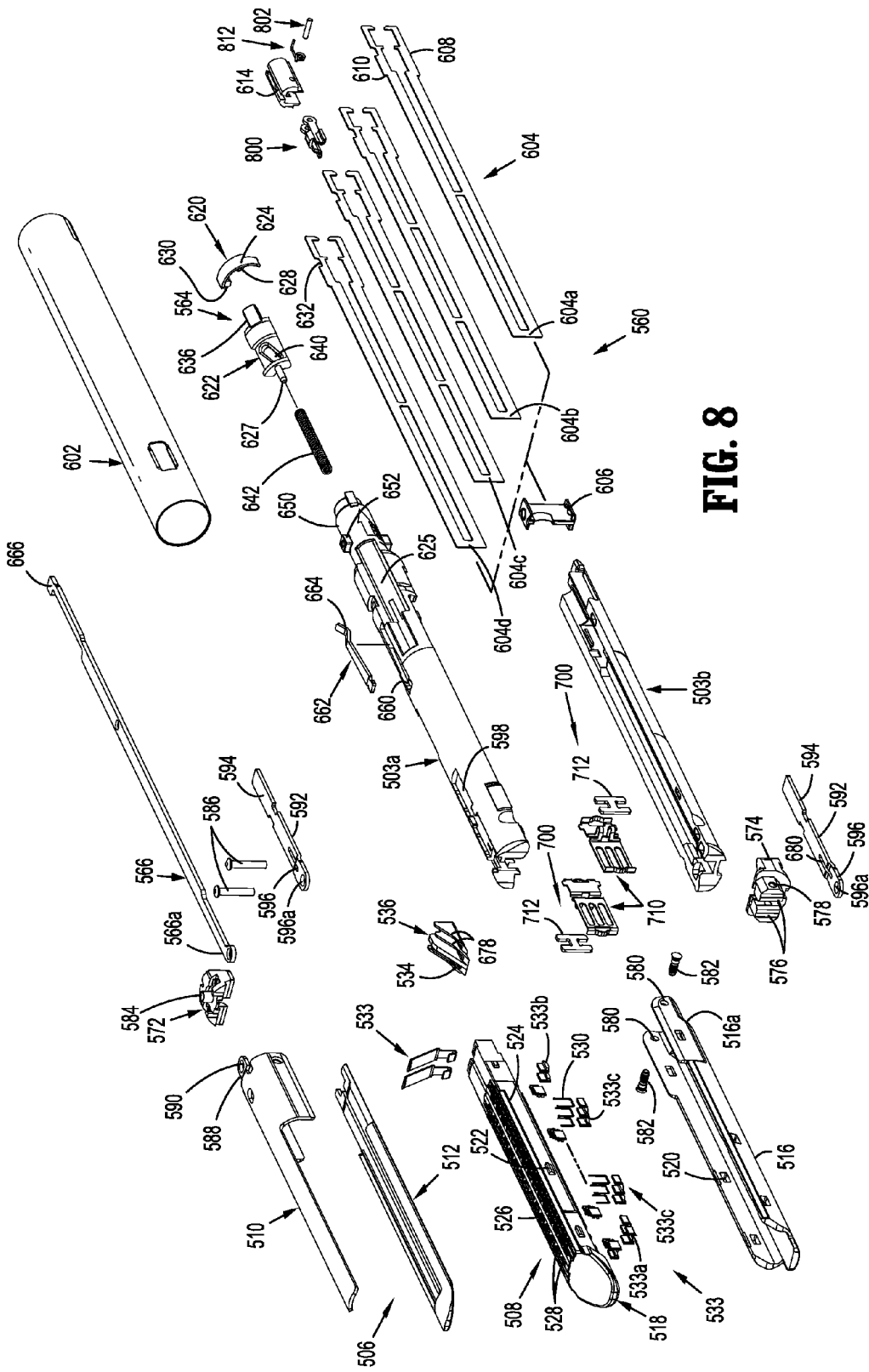
FIG. 8 is an exploded view of the loading unit according to certain embodiments of the present disclosure.

Referring to FIG. 8, a mounting assembly 572 is pivotally secured to the distal end of body 502, and is configured to be attached to the proximal ends of the jaws of the loading unit 20 such that pivotal movement of mounting assembly 572 about an axis perpendicular to the longitudinal axis of housing portion 502 effects articulation of the pair of jaws.

Referring to FIG. 8, mounting assembly 572 includes upper and lower mounting portions 584 and 574. Each mounting portion includes a bore on each side thereof dimensioned to receive bolts 582 for securing the proximal end of channel 516 thereto. A pair of coupling members 594 engage the distal end of housing portion 502 and engage the mounting portions. Coupling members 594 each include an interlocking proximal portion configured to be received in grooves 598 formed in the housing portion 502 to retain mounting assembly 572 and body 502 in a longitudinally fixed position in relation thereto.

A pair of blow out plates 710 are positioned adjacent the distal end of body 200 adjacent the distal end of axial drive assembly to prevent outward bulging of drive assembly during articulation of the pair of jaws. Each blow-out plate 710 includes a planar surface which is substantially parallel to the pivot axis of the pair of jaws and is positioned on a side of drive assembly to prevent outward bulging of drive member 604. Each blow-out plate includes a first distal end which is positioned in a respective first groove formed in mounting assembly 574 and a second proximal end which is positioned in a respective second groove formed in a distal end of housing 503b.

Staples 530 are disposed in the staple slots 528 and are driven out of those staple slots by pushers 533. The vertical portion 606a also extends through the slot in the anvil member 512 to locate the upper flange 606b on an upper surface of the anvil 512. A sled 536 is positioned in the staple cartridge initially in a proximal position, and has wedges 534 that engage the pushers 533. The pushers have camming surfaces (not shown) so that as the sled 536 is advanced by the drive beam 604 and clamping member 606, the sled will lift the pushers, driving the staples out of the slots 528, through tissue, and against staple forming recesses in the anvil 512. As the drive beam 604 and clamping member 606 is initially advanced, the upper flange rides along the ramped surface 516a to approximate the anvil assembly 506 with the cartridge assembly 508. As the staples are fired, the drive beam 604 and clamping member 606 continue to engage the anvil assembly and cartridge assembly to maintain the position of the anvil assembly and cartridge assembly during firing of the staples.

The loading unit 20 can include a first data connector for connection with a second data connector on the adapter assembly 100, to feed data back to a controller 9 in the handle portion 10. The first data connector can comprise a contact or contacts on the body 200 of the loading unit, whereas the second data connector can be one or more contacts arranged on the adapter assembly 100 to connect with the contacts of the first data connector. A memory unit is disposed in the loading unit and is connected to the first data connector. The memory unit can comprise an EEPROM, EPROM, or the like, contained in the body 200 and can hold information such as the type of loading unit, the size of the staples in the loading unit, the length of the staple line formed by the loading unit when the staples are fired, and information about whether the loading unit has already been fired. The second data connector is connected to the controller 9 in the handle assembly by wires, or leads, that extend through the adapter assembly, or via wireless connection. Alternatively, the memory unit of the loading unit can communicate wirelessly with the controller in the handle portion.

The memory unit can store the end of stroke of the axial drive assembly, or the length of the stroke, for the loading unit. This information can be used by the controller 9 to avoid over driving the axial drive assembly, which can damage the loading unit. In this way, the controller can receive the end of stroke or stroke length information, and halt the driving of the stapling drive cable 134 when the end of the stroke is reached. Alternatively, the controller 9 can be configured to detect when the axial drive assembly has reached the end of the stroke, and has fired all the staples in the staple line. The controller detects this, using sensors in the loading unit, or by monitoring the current in the motor assembly. For example, when the current in the motor assembly increases dramatically, or spikes, the operation of the motor assembly is halted.

The controller 9 can be an integrated circuit, analog or logic circuitry, and/or microprocessor, or an array of such components. The controller receives information from the loading unit memory unit, other sensors in the adapter assembly and/or loading unit, and can control the operation of the surgical device. For example, sensors can be used to detect the clamping forces at the cartridge assembly and anvil assembly. The controller can initiate a visual or audible alarm in the event that recommended forces are exceeded, or the controller can cease operation of the surgical device by halting the motor of the handle assembly. A removable memory chip or card can also be included.

Where loading units 20 having different staple line lengths are available for use with the surgical device, identifying the length of the staple line and using that information to control the operation of the surgical device can be useful. For example, the controller 9 receives the staple line length from the memory unit and through the first data connector on the loading unit. That information is compared with data from the memory unit 11 in the handle portion 10 to determine how far to drive the staple drive shaft 148 and avoid driving that shaft 148 too far, and potentially damaging the loading unit. The type of loading unit, and the staple line length, staple size, etc., can therefore be used to control the operation of the surgical device. The controller 9 can be programmed to reverse the direction that the stapling drive cable 134 is driven after the staple line length is reached, thereby reversing the direction of the stapling drive shaft 148 and allowing the jaws of the loading unit to open. Alternatively or additionally, sensors can be provided in the loading unit to determine the position of the sled 536, clamping member 606, and/or drive beam 604, and to reverse the direction of the motor when the end of the staple line has been reached.

The handle portion 10 supplies power to the motor assembly 5 through a battery, generator, or electrical socket in order to drive the rotation of the cables 134, 136. The amount of torque required to clamp the jaws of the loading unit onto tissue can be sensed, by monitoring the motor current. During clamping of tissue, during the initial movement of the clamping member 606 over the ramped surface 516a of the channel 516, the clamping member 606 exerts forces on the channel 516, and on the tissue being clamped between the cartridge assembly and anvil assembly. These forces can be detected by the controller 9, and characterized. For example, the force of the cartridge assembly in clamping tissue against the anvil 512 can be detected and compared to data in the memory unit 11 of the controller, and used to provide information to the surgeon. Also, this information can be saved and reported for later use. The handle portion 10 desirably has a display unit and/or indicator for displaying information or alerting the user of the surgical device. Additionally or alternatively, the device can include an audio component for sounding an audible alarm or recorded message. The display can be a light emitting diode, liquid crystal display or any other display.

An encoder or encoders can be used as one or more of the sensors of the surgical device. The encoder includes Hall effect devices mounted adjacent the drive shafts from the motors, to detect a magnet or magnets mounted on the shafts. In this way, the angular position of the drive shafts and their direction, as well as the position of the drive shafts, drive cables 134, 136, articulation drive bar 154, and/or stapling drive shaft 148 can be determined. It is contemplated that, in any of the embodiments disclosed herein, there are encoders or other sensors provided for the drive cables 134, 136, articulation drive bar 154, and/or stapling drive shaft 148. In any of the embodiments disclosed herein, current draw characteristics from the battery or batteries, and from the one or more motors of the motor assembly 5 are sensed. Other strain, force, and/or positional sensors in the end effector, adapter assembly, and/or handle portion are contemplated.

Sensors 211 can also be provided in the loading unit 20 to determine the gap between the staple cartridge 508 and anvil 512. The controller 9 can include tables of information that indicate the desired gap for a particular loading unit (based on staple size, staple line length, etc.) and can be used to prevent the firing of staples in the event that the desired gap cannot be achieved. For example, U.S. Patent Publication No. 2012/0211542, the entire disclosure of which is hereby incorporated by reference herein, discloses tissue management modes for controlling a surgical device and utilizes stored correlation tables. In any of the embodiments disclosed herein, the surgical device can include a controller and sensors in the adapter assembly 100, loading unit 20, and/or handle portion 10 that determine the clamping force, the gap between the cartridge 508 and anvil 512, whether the loading unit has been used, the type of loading unit, and/or the staple line length or size. The information is used to control the operation of the surgical device, provide some indication to the user, and/or is simply stored for later use.

In any of the embodiments disclosed herein, the loading unit has a mechanical feature for determining the type of cartridge 220, the staple line length, size of the staples, etc. The mechanical feature is a specially shaped bump, depression, or series of bumps or depressions, that are unique to that type of loading unit. The mechanical feature can have different shapes and/or textures, can determine staple size, staple line length, or both. It can also be used to determine other aspects of the loading unit, such as whether it is articulating or non-articulating, or whether a buttress material is being used. The mechanical feature can be a coating on the loading unit, that provides texture, a different frictional resistance, or some other aspect that can differentiate the type of loading unit.

Figure 9:
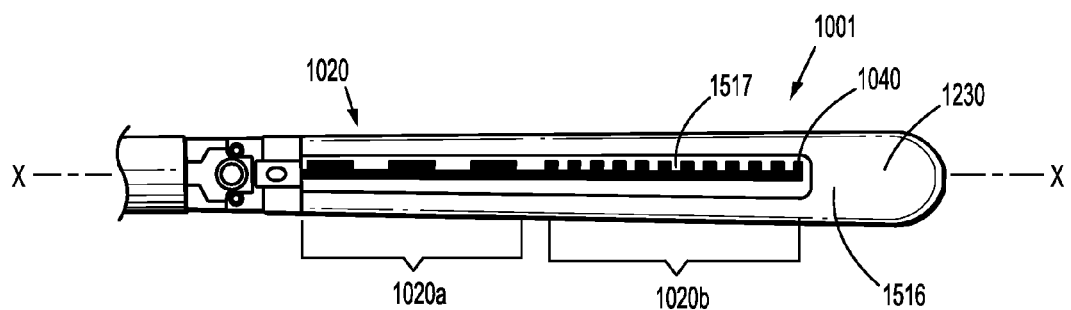
FIG. 9 is a top plan view of the loading unit according to certain embodiments of the present disclosure.

The mechanical feature 1020 is located on the loading unit at a location where the clamping member 606 engages the cartridge assembly 508, anvil assembly 506, or both. As shown in FIG. 9, a loading unit 1001 has an anvil assembly and cartridge assembly 1230. In the initial advancement of the clamping member 606, which can be the clamping member shown in FIGS. 6, 7 and 8, the clamping member lower flange 606c traverses the ramped surface 516a. Then, the clamping member proceeds to move down the surface of the channel 1516, as driven by the staple drive member 148. The mechanical feature or features 1020 provided on the channel 1516 change the force or torque at the motor. The change in force or torque is detected by the controller 9 of the handle portion and compared to data in the memory unit 11 of the controller. The end of stroke 1040 for the particular loading unit 1001 is determined. Using this information, the controller 9 determines that the loading unit 1001 has, for example, a 60 millimeter staple line length, and drives the stapling drive cable 134 a predetermined number of rotations, to drive the stapling drive shaft 148 the distance necessary for driving all of the staples, but not exceeding the length of the cartridge assembly.

For example, the linear force can be determined utilizing motor current, motor current limits, and/or revolutions per minute. Alternatively, strain gauges can be used. These measurements can be taken with sensors in the end effector, adapter assembly and/or handle portion.

In addition, it can be determined that the loading unit is an articulating loading unit, allowing the articulation drive cable 136 to be driven. If it is determined that the loading unit is not an articulating loading unit, the articulation drive cable 136 is prevented from being driven by not turning on the corresponding motor in the motor assembly 5. For example, a mechanical feature or features 1020 can be provided on the anvil 512 that identify the type of loading unit, staple line length, staple size, or identify the loading unit as articulating. Similarly, a mechanical feature or features 1020 can be provided on the channel 1218 and/or anvil surface that identify the loading unit as having a buttress preloaded onto the loading unit, or identify the loading unit as one that has a dissecting tip.

In any of the embodiments disclosed herein, the mechanical feature 1020 can be provided on the anvil assembly, cartridge assembly 1230, or both, in a pattern of recesses, protrusions, hills, valleys, or some combination of the foregoing. The physical features of the pattern of mechanical features 1020 change the force or torque at the motor assembly and are detected at the controller. In certain embodiments, the mechanical features 1020 have a first pattern 1020*a* and a second pattern 1020*b*. Two or more different patterns can be used, to expand the number of different loading units 1001 that can be indicated. In addition, the pattern or a change in the pattern of mechanical features 1020 can be used to indicate that the clamping member 606 is reaching the end of stroke 1040. The controller can be configured (programmed or structured or the like) to monitor the change in force or torque, and determine when the operation of the motor assembly 5 should be arrested. In this way, the driving of the axial drive assembly is halted before the axial drive assembly reaches the end of stroke 1040. For example, as shown in FIG. 9, the mechanical features 1020 have a first pattern 1020*a* and a second pattern 1020*b* that are different from each other in that they have different recesses or protrusions. For example, first pattern 1020*a* has recesses or protrusions that are longer in length than the recesses or protrusions of the second pattern 1020*b*. The controller is configured to determine the end of stroke 1040 for the particular loading unit 1001 based on the change in the torque or force detected by the controller. The velocity of the movement of the clamping member, as well as its position, can be determined, based on the indication provided by the mechanical feature.

For example, the loading unit 1001 has a cartridge assembly 1230 with a staple cartridge that defines a longitudinal axis X as shown in FIG. 9. The axial drive assembly is driven through the staple cartridge to fire the surgical staples as discussed above, in the longitudinal direction along the axis X. As the axial drive assembly is driven, the clamping member 606 lower flange 606*c* engages the channel 1516 and any mechanical features 1020 provided on the channel 1516. In this way, the lower flange 606*c* engages the first pattern 1020*a* of mechanical features first, and then engages the second pattern 1020*b* of mechanical features. The second pattern 1020*b* of mechanical features is disposed closer to a distal end of the channel 1516, and closer to the end of stroke 1040.

The channel 1516 defines a slot 1517 to allow the vertical portion 606*a* of the clamping member to pass through the slot 1517 so that the lower flange 606*c* can engage the channel 1516. A distal end of the slot 1517 is defined in the channel, and forms the end of stroke 1040. Attempting to drive the axial drive assembly past the distal end of the slot 1517, past the end of stroke 1040, can result in damaging the loading unit 1001, the adapter assembly, components of the handle assembly, etc.

In any of the embodiments disclosed herein, electronic sensors, optical sensors, magnetic sensors, and/or any other kind of sensors, can be used in addition to the mechanical feature 1020 to provide information about the particular loading unit and its use. In any of the embodiments disclosed herein, an electronic sensor, magnetic sensor, optic sensor, or other sensor, is provided on the upper flange 606*b*, anvil 512, channel 516, or any combination thereof, to indicate the type of loading unit, staple size, staple line length, other aspects of the loading unit, and/or whether the loading unit has been fired or previously used.

In any of the embodiments disclosed herein, the adapter assembly can include a sensor or identification chip, for any of the purposes discussed herein, including for identifying the type of adapter assembly or characteristics thereof. Electronic sensors, optical sensors, magnetic sensors, and/or any other kind of sensors can be used. Desirably, the sensor or chip communicates with the controller, which may be located in the handle portion, through wires or leads, or through wireless communication.

The sensors provided may include, in any of the embodiments disclosed herein, temperature sensors for measuring the internal temperature in or around the surgical device.

The controller comprises one or more microprocessors or chips, as discussed above. The controller can comprise more than one such chips or processors, and can be an array of such elements. Data for determining the type and characteristics of end effectors, adapter assemblies and/or handle portions can be stored in memory units in the form of graphs, charts, tables, arrays, or the like. This can be used in conjunction with other systems provided for the surgical device.

Furthermore, the circular stapling loading unit 30 and transverse stapling loading unit 40 have driver members like the clamping member 606 and drive beam 604 described above that can be used with mechanical features 1020 to determine the type of loading unit, size of staples, length or diameter of the staple line, etc. Mechanical features on the driven elements of these stapler components can be used to identify the information discussed herein.

Information communicated through a feedback loop of the controller can be used to determine functional modes for each unique end effector, adapter assembly, and/or handle portion. Based on an end effector or loading unit ID and current firing conditions, performance of the system can be dynamically adjusted to achieve improved outcomes. These settings can be pre-determined or intelligently adapter by the controller during operation.

One example implementing this would be adjusting the torque output when an unknown buttress material was detected to be in use.

The mechanical features can be located in a variety of positions. Examples can include, but are not limited to the following.

In a circular stapler device, such as an EEA stapler, the mechanical features are provided along any component or components which move during operation. Mechanical features can be formed on the clamp shaft and/or staple shaft. The clamp shaft has the largest stroke and can be used to collect both positional information and force information. For example, the controller could monitor how a component deforms under the applied load and measuring this deformation using the feedback loop sensors and the controller.

In a linear endoscopic device, such as an Endo GIA stapler, the location of the mechanical features in the end effector or loading unit can include, but is not limited to, mechanical features on the sides of the drive beam, which would be read by a sensor as they pass. This pattern can be applied symmetrically on both sides, or asymmetrically to increase bandwidth of the signal.

Figure 10A:
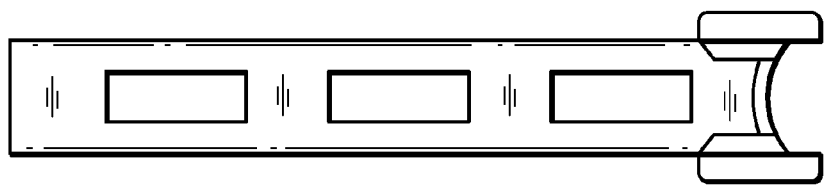
FIG. 10A is a side elevation view of a drive assembly according to embodiments of the present disclosure.

Mechanical features on the top and or bottom of the knife bar (see FIG. 10) can be such that a sensor can detect the features along the surface. The drive bar may have a plurality of openings or windows which can be used in lieu of or in addition to mechanical features. A conventional physical sensor, or a photocell, could be used to determine such windows have passed, or how many have passed, or how quickly they have passed. In any of the embodiments disclosed herein, a conventional physical sensor, or a photocell, could be used to determine that the mechanical features have passed, and/or how many have passed, and/or how quickly they have passed.

Figure 10B:
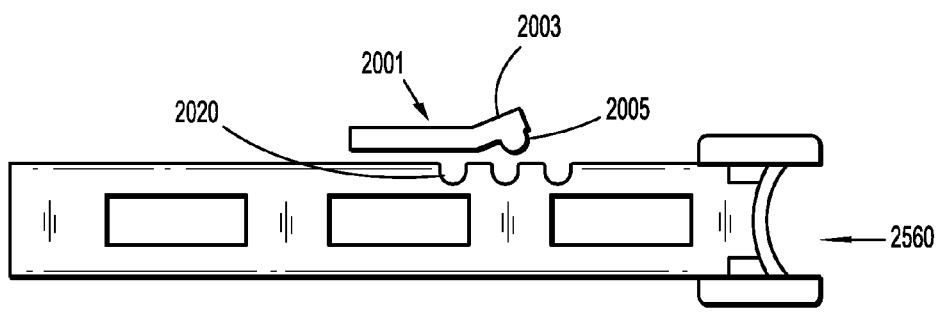
FIG. 10B is a side elevation view of a drive assembly according to embodiments of the present disclosure.

Furthermore, the bottom portion of the clamping member, the lower flange 606c, or a separate member that forms the bottom portion, can include the mechanical features. Such mechanical features can be on the surface that engages the channel, or on the sides of the flange. The channel itself could include mechanical features, or the sides of the drive beam can include such features. See FIGS. 10A and 10B. The loading unit may include a sensing member 2001 being attached to the loading unit housing at one end, and having an opposite free end 2003. The member 2001 is flexible and includes a protrusion 2005 on the free end 2003. As the drive beam or member 2560 is advanced through the staple cartridge and anvil, the protrusion interacts with mechanical features 2020 on the drive beam. As shown in FIG. 10B, the mechanical features 2020 may be recesses on the drive beam. In other embodiments, a photocell or other sensor detects, counts, records, or otherwise recognizes the mechanical features as a means to identify the loading unit, characteristics thereof, the end of stroke, and/or the velocity of the drive bar. The remaining components of the loading unit having the drive beam 2560 can be as described above in connection with loading unit 20.

While the present invention has been described and illustrated in connection with certain embodiments, it is not the intention of the applicant to restrict or in any other way limit the scope of the claims to such detail. Additional advantages and modifications will be readily apparent to those skilled in the art.

What is claimed is:

1. A loading unit for a surgical stapling device, comprising:
   a cartridge assembly and an anvil assembly, the cartridge assembly including a channel and a staple cartridge having a plurality of surgical staples therein;
   an axial drive assembly with a clamping member, the clamping member having an upper flange for engaging the anvil assembly, and a lower flange for engaging the channel;
   mechanical features defined in the channel for indicating an end of stroke for the axial drive assembly, the mechanical features having a first pattern and a second pattern;
   a motor coupled to the axial drive assembly, the motor configured to move the axial drive assembly through the staple cartridge to drive the staples out of the staple cartridge and against the anvil assembly; and
   a controller coupled to the motor and configured to determine the end of stroke based on a change in torque at the motor in response to the clamping member engaging the mechanical features.

2. The loading unit according to claim 1, wherein the staple cartridge has a plurality of staple retaining recesses and the surgical staples are disposed in the staple retaining recesses.

3. The loading unit according to claim 2, wherein the staple retaining recesses are arranged in linear rows.

4. The loading unit according to claim 1, wherein the axial drive assembly includes a drive beam.

5. The loading unit according to claim 1, further comprising a sensor for determining a gap between the anvil assembly and the cartridge assembly.

6. A surgical stapling device, comprising an elongate portion and a loading unit according to claim 1.

7. The surgical stapling device according to claim 6, further comprising a handle portion.

8. The surgical stapling device according to claim 1, wherein the controller is configured to determine the end of stroke.

9. The surgical stapling device according to claim 8, wherein the first pattern of mechanical features has mechanical features of a different size than a size of the mechanical features of the second pattern.

10. The loading unit according to claim 1, wherein the staple cartridge defines a longitudinal axis and staple retaining recesses arranged in linear rows along the longitudinal axis.

11. The loading unit according to claim 1, wherein the channel defines a slot.

12. The loading unit according to claim 11, wherein a distal end of the slot forms the end of stroke.

13. The loading unit according to claim 12, wherein the second pattern of mechanical features is closer to the distal end of the slot than the first pattern of mechanical features.

* * * * *